United States Patent [19]

Yazawa et al.

[11] Patent Number: 5,202,462

[45] Date of Patent: Apr. 13, 1993

[54] PROCESS FOR PRODUCING A HALOMETHYL PIVALATE

[75] Inventors: Naoto Yazawa, Shizuoka; Keinosuke Ishikame, Tokyo, both of Japan

[73] Assignee: Ihara Chemical Industry Co., Ltd., Tokyo, Japan

[21] Appl. No.: 920,529

[22] Filed: Jul. 28, 1992

Related U.S. Application Data

[63] Continuation of Ser. No. 686,921, Apr. 18, 1991, abandoned.

[30] Foreign Application Priority Data

Apr. 20, 1990 [JP] Japan .................. 2-104544

[51] Int. Cl.$^5$ .................................................. C07C 69/62
[52] U.S. Cl. ............................................................... 560/236
[58] Field of Search ................................................. 560/236

[56] References Cited

U.S. PATENT DOCUMENTS

| | | | |
|---|---|---|---|
| 3,992,432 | 11/1976 | Napier | 560/236 |
| 4,421,675 | 12/1983 | Sawicki | 560/236 |
| 4,699,991 | 10/1987 | Arkles | 560/236 |

FOREIGN PATENT DOCUMENTS

| | | | |
|---|---|---|---|
| 2245457 | 3/1973 | Fed. Rep. of Germany. | |
| 3152341 | 6/1988 | Japan | 560/236 |

OTHER PUBLICATIONS

Chemical Abstracts, vol. 107, No. 17, Oct. 26, 1987, Andreev et al: "Chloromethyl pivalate." p. 664, Abstract No. 153938q.

Chemical Abstracts, vol. 101, No. 23, Dec. 3, 1984, Binderup et al: "Chlorosulfates as reagents in the synthesis of carboxylic acid esters . . . ", p. 563, Abstract No. 210 048b.

*Primary Examiner*—Arthur C. Prescott
*Attorney, Agent, or Firm*—Oblon, Spivak, McClelland, Maier & Neustadt

[57] ABSTRACT

A process for producing a halomethyl pivalate which comprises reacting an aqueous solution of a metal salt of pivalic acid with a dihalomethane selected from the group consisting of bromochloromethane, chloroiodomethane and bromoiodomethane in the presence of a phase transfer catalyst.

14 Claims, No Drawings

PROCESS FOR PRODUCING A HALOMETHYL PIVALATE

This application is a continuation of application Ser. No. 07/686,921, filed Apr. 18, 1991 now abandoned.

The present invention relates to a process for producing a halomethyl pivalate which is useful as a starting material for cephem antibiotics (which are disclosed, for example, in Japanese Unexamined Patent Publication No. 19593/1987).

Heretofore, as a process for producing a halomethyl pivalate, it has been known to conduct so-called Blanc-Quelet reaction wherein formaldehyde and a hydrogen halide are reacted with pivalic acid in the presence of a catalyst such as aluminum chloride or zinc chloride. However, such a process has a problem that highly poisonous chloromethyl methyl ether and bis(chloromethyl)ether (hereinafter referred to simply as halomethyl ethers) are produced as by-products.

It is an object of the present invention to provide a process for producing a halomethyl pivalate which does not produce highly poisonous halomethyl ethers as byproducts produced in conventional methods and which is useful for practical industrial application.

The present inventors have conducted extensive researches to develop a process for producing a halomethyl pivalate which does not produce highly poisonous halomethyl ethers. As a result, it has been found that the object of the present invention can be attained by using a dihalomethane having halogen atoms different from each other in a process for producing a halomethyl pivalate by reacting an aqueous solution of a metal salt of pivalic acid with a dihalomethane in the presence of a phase transfer catalyst. The present invention is based on this discovery.

Namely, the present invention provides a process for producing a halomethyl pivalate which comprises reacting an aqueous solution of a metal salt of pivalic acid with a dihalomethane selected from the group consisting of bromochloromethane, chloroiodomethane and bromoiodomethane in the presence of a phase transfer catalyst.

Now, the present invention will be described in detail with reference to the preferred embodiments.

As the aqueous solution of a metal salt of pivalic acid to be used as a starting material in the present invention, an aqueous solution of an alkali metal or alkaline earth metal salt of pivalic acid may be mentioned. As the alkali metal or alkaline earth metal salt of pivalic acid, sodium, potassium, magnesium or barium salt of pivalic acid may be mentioned.

Such a metal salt of pivalic acid can be readily produced by reacting pivalic acid with an aqueous solution of a hydroxide, carbonate or hydrogen carbonate of an alkali metal or alkaline earth metal. The aqueous solution of a metal salt of pivalic acid thus obtained may be used as it is in the form of the aqueous solution. Alternatively, pivalic acid and a metal salt of an alkali metal or alkaline earth metal are reacted directly in the reaction system to obtain an aqueous solution of the metal salt of pivalic acid.

Further, water is used at least in an amount capable of stirring, preferably at least in an amount capable of dissolving the inorganic salt formed.

Moreover, there is no particular restriction as to the order to add pivalic acid, the base, the dihalomethane and the phase transfer catalyst.

According to the present invention, it is essential to have a phase transfer catalyst present during the reaction of the aqueous solution of metal salt of pivalic acid with the dihalomethane. As the phase transfer catalyst, any catalyst which is usually called a phase transfer catalyst can be employed. For example, quaternary onium salts such as a quaternary ammonium salt, a quaternary pyridinium salt and a quaternary phosphonium salt are usually used. They may be used alone or in combination. Among them, preferred are tetrabutylammonium bromide, tetrabutylammonium chloride, trioctylmethylammonium chloride and trioctylmethylammonium bromide which are readily obtainable from the industrial viewpoint.

In the process of the present invention, the phase transfer catalyst is used in an amount of from 0.001 to 1 mol, preferably from 0.005 to 0.2 mol, per mol of the metal salt of pivalic acid.

Further, the dihalomethane selected from the group consisting of bromochloromethane, chloroiodomethane and bromoiodomethane, which is to be reacted with the aqueous solution of the metal salt of pivalic acid, is used in an amount of from 1 to 100 mols, preferably from 10 to 50 mols, per mol of the aqueous solution of the metal salt of pivalic acid.

In the process of the present invention, a nonaqueous inert organic solvent such as benzene, toluene and diethyl ether can be used as the case requires.

Now, a specific embodiment suitable for the process of the present invention, will be described. Firstly, a phase transfer catalyst, an aqueous solution of a metal salt of pivalic acid and a dihalomethane selected from the group consisting of bromochloromethane, chloroiodomethane and bromoiodomethane are mixed and reacted in predetermined proportions. There is no particular restriction on the reaction temperature, and it is usually from 0° C. to the reflux temperature of the reaction system. The reaction time depends on the starting materials employed, the reaction temperature, the catalyst, etc., and it is usually about from 1 to 10 hours. The reaction can be conducted under atmospheric pressure or elevated pressure. After completion of the reaction, the reaction mixture is allowed to stand to have an aqueous phase and an oil phase separated. Then, only the oil phase is collected, washed and distilled off, whereby a halomethyl pivalate is obtained.

In the process of the present invention, the pivalic acid can be quantitatively recovered from the distillation residue by subjecting bis(pivaloyloxy)methane produced as by-product to hydrolysis with an alkali or acid, and the pivalic acid recovered can be reused. Accordingly, the process of the present invention is so efficient that the pivalic acid is consumed only for the formation of the halomethyl pivalate.

According to the process of the present invention wherein an aqueous solution of a metal salt of pivalic acid is reacted with a dihalomethane selected from the group consisting of bromochloromethane, chloroiodomethane and bromoiodomethane in the presence of a phase transfer catalyst, it is possible to produce halomethyl pivalate in good yield and without production of halomethyl ethers as by-products. Further, the pivalic acid can be recovered quantitatively by means of hydrolysis of bis(pivaloyloxy)methane produced as by-product, and the recovered pivalic acid can be reused. Thus, the process of the present invention is suitable as an industrial process for the production of halomethyl pivalate.

Now, the present invention will be described in further detail with reference to examples. However, it should be understood that the present invention is by no means restricted by these specific examples.

EXAMPLE 1

Into a 200 ml reaction flask equipped with a condenser, a thermometer and a stirrer, 161.7 g of bromochloromethane, 5.1 g of pivalic acid, a 48% sodium hydroxide aqueous solution and 0.5 of tetrabutylammonium bromide were introduced and reacted for 2.5 hours. The conversion and the selectivity for chloromethyl pivalate are shown in Table 1. (Neither chloromethyl methyl ether nor bis(chloromethyl)ether was detected from the above reaction solution.)

After completion of the reaction, the reaction solution was allowed to stand, and the oil phase separated, was collected, washed and distilled off to obtain 153.6 g of bromochloromethane as a fraction having a boiling point of 67° C. (yield: 95%). The distillation was further conducted under reduced pressure at a level of 50 mmHg to obtain 2.58 g of chloromethyl pivalate as a fraction having a boiling point of from 70 to 72° C. The yield was 34.3% based on pivalic acid.

EXAMPLES 2–5

The reaction was conducted in the same manner as in Example 1 except that the amount of water, a 48% sodium hydroxide aqueous solution and tributylammonium bromide (TBAB) and the reaction temperature were changed as indicated in Table 1. The conversion of the reaction solution and the selectivity for chloromethyl pivalate are shown in Table 1.

TABLE 1

| Example | 1 | 2 | 3 | 4 | 5 |
|---|---|---|---|---|---|
| H$_2$O (g) | 10 | 10 | 25 | 10 | 10 |
| 48% NaOH (g) | 4.2 | 4.2 | 4.2 | 4.2 | 4.6 |
| TBAB[1] (g) | 0.5 | 0.5 | 0.5 | 0.3 | 0.5 |
| Reaction Temperature (°C.) | 59–61 | 40 | 59–61 | 59–61 | 59–61 |
| Conversion (%) | 47.9 | 19.3 | 52.1 | 41.8 | 50.7 |
| Selectivity (%) | 71.3 | 88.4 | 71.1 | 75.3 | 69.8 |
| Selectivity for Bis-product[2] (%) | 28.4 | 11.6 | 28.9 | 24.7 | 30.2 |

[1] Tributylammonium bromide
[2] Bis(pivaloyloxy)methane

EXAMPLES 6–8

The reaction was conducted in the same manner as in Example 1 except that bases and catalysts as identified in Table 2 were used or a solvent was added. The conversion of the reaction solution and the selectivity for chloromethyl pivalate are shown in Table 2.

TABLE 2

| Example | 6 | 7 | 8 | COMPARATIVE EXAMPLE |
|---|---|---|---|---|
| H$_2$O (g) | 10 | 10 | 10 | 10 |
| Base (g) | NaOH[1] 4.2 | Na$_2$CO$_3$ 2.7 | NaOH[1] 4.2 | NaOH[1] 4.2 |
| Catalyst (g) | TBAB[2] 0.5 | TBAB[2] 0.5 | TOMAC[3] 0.4 | TBAB[2] 0.5 |
| Solvent (g) | Toluene 10 g | | | |
| Reaction Temperature (°C.) | 59–61 | 59–61 | 59–61 | 59–61 |
| Conversion (%) | 45.3 | 48.0 | 53.2 | 48.2 |
| Selectivity (%) | 72.0 | 70.4 | 68.7 | 0 |
| Selectivity for Bis-product[4] (%) | 28.0 | 29.6 | 31.2 | 100 |

[1] 48% sodium hydroxide aqueous solution
[2] Tributylammonium bromide
[3] Trioctylmethylammonium chloride
[4] Bis(pivaloyloxy)methane In Tables 1 and 2, the selectivity and the selectivity for bis product were calculated as follows:

$$\text{Selectivity} = \frac{\text{Yield of halomethyl pivalate}}{\text{Conversion of pivalic acid}}$$

$$\frac{\text{Selectivity for}}{\text{bis-product}} = \frac{\text{Yield of bis-product}}{\text{Conversion of pivalic acid}}$$

COMPARATIVE EXAMPLE

The reaction was conducted in the same manner as in Example 1 except that 217.3 g of dibromomethane was used instead of bromochloromethane. The results thus obtained are shown also in Table 2.

REFERENCE (Recovery of pivalic acid in Example 1)

The aqueous phase of the reaction solution was acidified with hydrochloric acid, and then extracted with diethyl ether. The extract was washed, dried and concentrated to obtain 2.6 g of the starting material pivalic acid (which corresponds to 51% of the pivalic acid introduced). Further, into the distillation residue, 5 g of a 24% sodium hydroxide aqueous solution was added and heated at 90° C. for 2 hours under stirring. Then, the solution was cooled and acidified with hydrochloric acid. The solution was extracted with ethyl ether, and the extract was washed, dried and concentrated to obtain 0.7 g of the starting material pivalic acid (which corresponds to 13.7% based on the amount introduced).

Accordingly, 98.5% of pivalic acid which was not used for production of chloromethyl pivalate, was recovered.

We claim:

1. A process for producing a halomethyl pivalate which comprises reacting an aqueous solution of a metal salt of pivalic acid with a dihalomethane selected from the group consisting of bromochloromethane, chloroiodomethane and bromoiodomethane in the presence of a phase transfer catalyst.

2. The process according to claim 1, wherein the phase transfer catalyst is at least one member selected from the group consisting of a quaternary ammonium salt, a quaternary pyridinium salt and a quaternary phosphonium salt.

3. The process according to claim 1, wherein the phase transfer catalyst is at least one member selected from the group consisting of tetrabutylammonium bromide, tetrabutylammonium chloride, trioctylmethylammonium chloride and trioctylmethylammonium bromide.

4. The process according to claim 1, wherein the metal salt is an alkali metal or alkaline earth metal salt.

5. The process according to claim 1, wherein the phase transfer catalyst is used in an amount of from 0.001 to 1 mol per mol of the metal salt of pivalic acid.

6. The process according to claim 1, wherein the dihalomethane is used in an amount of from 1 to 100 mols per mol of the metal salt of pivalic acid.

7. The process according to claim 1, wherein the reaction is conducted at a temperature of from 0° C. to the reflux temperature of the reaction system.

8. The process according to claim 1, wherein said aqueous solution of a metal salt of pivalic acid is reacted with 1–100 mols of said dihalomethane in the presence of 0.001–1 mol of a phase transfer catalyst selected from the group consisting of quaternary ammonium salts and quaternary phosphonium salts per mol of said metal salt of pivalic acid at a temperature of from 0° C. to the reflux temperature of the reaction system, and wherein the selectivity of said process is at least 68.7% calculated as the yield of halomethyl pivalate/conversion of pivalic acid.

9. A process for processing a halomethyl pivalate which comprises reacting an aqueous solution of a metal salt of pivalic acid with a dihalomethane selected from the group consisting of bromochloromethane, chloroiodomethane and bromoiodomethane in the presence of a phase transfer catalyst selected from the group consisting of quaternary ammonium salts, and quaternary phosphonium salts.

10. A process for producing a halomethyl pivalate composition containing reduced amounts of bis(pivaloyloxy)methane, comprising reacting an aqueous solution of a metal salt of pivalic acid at a temperature ranging from 0° C. to the reflux temperature of the reaction system with a dihalomethane selected from the group consisting of bromochloromethane, chloroiodomethane and bromoiodomethane in an amount of 1 to 100 mols of said dihalomethane per mol of said metal salt of pivalic acid in the presence of 0.01–1 mol of a phase transfer catalyst selected from the group consisting of quaternary ammonium salts and quaternary phosphonium salts to obtain a halomethyl pivalate composition wherein the selectivity is at least 68.7% calculated as the yield of halomethyl pivalate conversion of pivalic acid.

11. The process of claim 8, wherein said quaternary ammonium salt is a quaternary pyridium salt.

12. The process of claim 8, wherein 10–50 mols of dihalomethane per mol of said metal salt of pivalic acid is reacted with said aqueous solution.

13. The process of claim 10, wherein said quaternary ammonium salt is a quaternary pyridium salt.

14. The process of claim 10, wherein 10–50 mols of said dihalomethane per mol of said metal salt of pivalic acid is reacted with said aqueous solution.

* * * * *